(12) United States Patent
Adams et al.

(10) Patent No.: US 9,249,232 B2
(45) Date of Patent: Feb. 2, 2016

(54) FRAMEWORK SELECTION

(75) Inventors: Ralph Adams, Slough (GB); Alastair David Griffiths Lawson, Slough (GB); Andrew George Popplewell, Slough (GB); Kerry Louise Tyson, Slough (GB)

(73) Assignee: UCB BioPharma SPRL, Brussels (BE)

( * ) Notice: Subject to any disclaimer, the term of this patent is extended or adjusted under 35 U.S.C. 154(b) by 1030 days.

(21) Appl. No.: 12/307,051

(22) PCT Filed: Jun. 26, 2007

(86) PCT No.: PCT/GB2007/002400
§ 371 (c)(1),
(2), (4) Date: Sep. 3, 2009

(87) PCT Pub. No.: WO2008/003931
PCT Pub. Date: Jan. 10, 2008

(65) Prior Publication Data
US 2009/0326203 A1 Dec. 31, 2009

(30) Foreign Application Priority Data
Jul. 3, 2006 (GB) .................................. 0613209.6

(51) Int. Cl.
C40B 30/04 (2006.01)
C07K 16/00 (2006.01)
C07K 16/46 (2006.01)

(52) U.S. Cl.
CPC .............. *C07K 16/464* (2013.01); *C07K 16/465* (2013.01); *C07K 2317/24* (2013.01); *C07K 2317/92* (2013.01)

(58) Field of Classification Search
CPC ...................................................... A61K 39/395
USPC ...................... 530/387.3; 424/133.1; 435/69.1
See application file for complete search history.

(56) References Cited

U.S. PATENT DOCUMENTS

2004/0076627 A1    4/2004    Adair

FOREIGN PATENT DOCUMENTS

WO    WO03105782    12/2003

OTHER PUBLICATIONS

Foote, J. et al.; Antibody Framework Residues Affecting the Conformation of the Hypervariable Loops, Journal of Molecular Biology, Jan. 1992, pp. 487-499, vol. 224, London.
International Search Report dated Oct. 23, 2007.

*Primary Examiner* — Yan Xiao
(74) *Attorney, Agent, or Firm* — McDonnell Boehnen Hulbert & Bergoff LLP

(57) ABSTRACT

The present invention relates to improved methods for the selection of appropriate human acceptor framework regions for non-human (donor) antibodies and methods for obtaining humanized antibodies of high affinity using such acceptor frameworks.

10 Claims, No Drawings

200
FRAMEWORK SELECTION

This is a National Stage of International Application No. PCT/GB07/02400, filed Jun. 26, 2007.

The present invention relates to improved methods for the selection of appropriate human acceptor framework regions for non-human (donor) antibodies and methods for obtaining humanized antibodies of high affinity using such acceptor frameworks. The invention also relates to humanized antibodies produced using these methods.

Immunoglobulins are Y-shaped molecules comprising two identical heavy chains and two identical light chains. Disulfide bonds link together the heavy and light chain pairs as well as the two heavy chains. Each chain consists of one variable domain that varies in sequence and is responsible for antigen binding, these are known as the $V_H$ and $V_L$ domains for the heavy and light chains respectively. In the light chain there is a single constant domain (CL) and in the heavy chain there are three (CH1, CH2 and CH3), such molecules being whole antibodies.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated. It should be noted that the Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

There are three regions within the variable domains that are hypervariable in sequence set within four more highly conserved framework regions. These hypervariable regions are primarily responsible for antigen recognition and are referred to as 'complementarity-determining regions' (CDRs).

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 1987, 196:901-917), the loop equivalent to CDR-H1 extends from residue 26 to residue 32. Thus 'CDR-H1', as used herein, also includes a CDR located at residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

The high specificity and affinity of antibodies make them ideal diagnostic and therapeutic agents, particularly for modulating protein:protein interactions. Whole antibodies and antibody fragments are proving to be versatile therapeutic agents, as seen by the recent success of products such as ReoPro (chimeric antibody Fab fragment), Rituxan (chimeric IgG1), Remicade™ (chimeric IgG1), Herceptin (humanized IgG1), and Humira (human IgG1). Of particular interest are humanized antibodies, which are aimed at reducing or eliminating the inherent immunogenicity associated with non-human monoclonal antibodies.

The earliest work on humanizing antibodies by CDR-grafting was carried out on monoclonal antibodies recognising synthetic antigens such as the hapten, NP (EP0239400 and Jones et al., 1986, Nature 321:522-525). However, examples in which a mouse monoclonal antibody recognising lysozyme and a rat monoclonal antibody recognising an antigen on human T cells were humanized by CDR-grafting have been described (Verhoeyen et al., 1988, Science 239:1534; Riechmann et al., 1988, Nature 332:323-327). Riechmann et al., found that transfer of the CDRs alone (as defined by Kabat et al., 1987, in Sequences of Proteins of Immunological Interest, US Department of Health and Human Services, NIH, USA; Wu et al., 1970, J. Exp. Med. 132:211-250) was not sufficient to provide satisfactory antigen-binding activity in the CDR-grafted product. Thus, a problem exists in that CDR-only transfer does not always result in maintenance of the integrity of the three dimensional structure of the antigen binding site, the result being a loss of antigen-binding activity. It was found that a number of acceptor framework residues have to be altered so that they correspond to those of the donor framework region (see, for example, Riechmann et al., above). Protocols for selecting residues in the acceptor framework regions that may need to be changed are set forth in WO 90/07861 and WO 91/09967.

Previously, investigators screened multiple potential donor antibodies to determine the one with the appropriate binding characteristics, and humanized this antibody using CDR-transfer onto a human framework. A number of reviews discussing CDR-grafted antibodies have been published, including Vaughan et al. (1998, Nature Biotech. 16:535-539). However, transfer of the CDRs of a high affinity monoclonal antibody onto even a closely matched, homologous human acceptor framework does not reliably produce a humanized antibody with the appropriate binding and functional characteristics. This invention recognizes that the performance of the CDRs in their native frameworks may not equate to the performance of the same CDR sequences in human frameworks. Thus, for example, a mouse monoclonal antibody with an affinity of 50 pM for a given antigen may, once humanized by CDR transfer, have an affinity of 500 pM, whereas another mouse monoclonal antibody, with an affinity of 100 pM for the same antigen, may retain all this activity or even increase affinity in the CDR-transferred format. The important consideration is the performance of the CDRs in the final human framework, not in the original, native framework. Consequently, the invention enables the production of a humanized antibody of high affinity without regard for the affinity of the original donor antibody. The present invention utilizes the whole range of variable regions of multiple donor antibodies. For example, the large numbers of donor antibodies provided by using the selected lymphocyte antibody method (SLAM; see Babcook et al., 1996, Proc. Natl. Acad. Sci, 93, 7843-7848; WO 92/02551; WO2004106377) are fully utilized using the methods of the invention. Thus, provided is a rapid method for testing a large number of CDRs in human frameworks with a view to obtaining one or more humanized antibodies with the appropriate binding and functional characteristics, and specifically, a high affinity. The invention, thus, integrates humanization into the variable region discovery process and provides a less time-consuming and more reliable method for obtaining a high affinity humanized antibody, preferably wherein only the CDRs of the donor antibody have been transferred to the acceptor framework.

In EP0460167, Adair et al. detail a hierarchy of donor and acceptor amino acid residues that are deemed essential for the production of humanized antibodies. They do not suggest the hierarchy of residues presented in the invention disclosed herein. The invention disclosed herein hence provides a simpler and faster method for dealing with large numbers of donor antibodies and their selection for humanization.

Accordingly, provided is a method for obtaining at least one humanized antibody with specificity for a selected antigen comprising:
(1) providing multiple donor antibody $V_H$ and/or $V_L$ region sequences, each with specificity for the selected antigen;
(2) selecting an appropriate human acceptor framework $V_H$ and/or $V_L$ region sequence for each donor sequence;
(3) transferring at least one CDR selected from the $V_H$ and/or $V_L$ region of each donor antibody onto each of the selected appropriate human acceptor framework sequences to obtain a panel of humanized antibody sequences;
(4) expressing the humanized antibody sequences;
(5) screening the expressed antibody for antigen-binding activity; and
(6) selecting at least one high affinity humanized antibody.

In one embodiment, step (3), above, includes the additional transfer of one or more residues (donor residues) from the donor sequence onto the selected appropriate human acceptor framework sequence.

The term "panel of humanized antibody sequences" includes at least 5, more preferably at least 10 to 20, and even more preferably at least 20 to 30, 40 or 50 or more antibodies. The multiple humanized antibodies may then simply be expressed and screened for antigen-binding and one or more high affinity humanized antibodies selected. Such antibodies may be used for development into therapeutic antibodies.

In one example, the methods of the present invention permit the expression of humanized antibodies without the need to produce chimeric, intermediate antibodies. Thus, there is no need to monitor the progress of the antigen-binding activity of the multiple donor antibodies, such is the reliability of the method in enabling the production of high affinity humanized antibodies. Hence, the invention utilizes multiple donor antibodies with specificity for a selected antigen and permits the filtering of these down to a manageable number for humanization (the panel).

Monoclonal donor antibodies for use in the methods of the invention can be obtained from any source, for example, from hybridoma cells. In particular, the invention can efficiently utilize the output of the SLAM process for obtaining monoclonal antibody variable domain sequences. Thus, most preferably the donor antibodies for use in the invention have been generated using SLAM (see above) and the method described in WO2004106377.

Monoclonal antibodies can be of any species and include monoclonal immunoglobulin molecules and immunologically active portions of said immunoglobulin molecules, i.e. molecules that contain an antigen-binding site (epitope-binding site) that specifically binds an antigen. The antibodies utilised in the invention can be of any class (e.g. IgG, IgE, IgM, IgD or IgA) or subclass of immunoglobulin molecule.

A humanized antibody includes an antibody produced by CDR-only transfer or by CDR-transfer plus transfer of one or more donor residues, and thus includes an antibody molecule wherein the heavy and/or light chain contains one or more CDRs from a donor non-human antibody (e.g. murine or rat or other monoclonal antibody) grafted onto a heavy and/or light chain variable region framework of a human antibody. The humanized antibody sequences utilized in the invention may be whole antibodies, or may be fragments, such as Fab fragments, Fab' and F(ab')2 fragments, scFvs, and epitope-binding fragments of any of the above (see, for example, Holliger and Hudson, 2005, Nature Biotech. 23(9):1126-1136). Thus, the humanized antibodies provided by the methods of the invention can comprise a $V_H$ or a $V_L$ domain, but more preferably comprise a $V_H$ and $V_L$ domain and, even more preferably, comprise two $V_H$ and two $V_L$ domains. In one example, the humanized antibodies comprise one CDR transferred from a donor antibody, for example CDR-H1, CDR-H2 or CDR-H3, most preferably, CDR-H3. In another example, the humanized antibodies comprise one CDR transferred from a donor antibody, for example CDR-L1, CDR-L2, or CDR-L3. In yet another example, the humanized antibodies comprise at least two of CDR-H1, CDR-H2, and CDR-H3 (preferably CDR-H3 and one other), and more preferably comprise all three of CDR-H1, CDR-H2, and CDR-H3 from a donor antibody. In a further example, the humanized antibodies comprise at least two of CDR-L1, CDR-L2, and CDR-L3, and more preferably comprise all three of CDR-L1, CDR-L2, and CDR-L3 from a donor antibody. In a preferred example, the humanized antibodies comprise a $V_H$ and a $V_L$ region wherein CDR-H1, CDR-H2, CDR-H3, CDR-L1, CDR-L2, and CDR-L3 have been transferred from a donor antibody. Thus, the skilled person will appreciate that a panel of humanized antibodies may contain humanized antibodies where one, two, three, four, five or all six CDRs from a donor antibody have been transferred. One or more antibodies in the panel may differ in the number of CDRs that have been transferred. Most preferably, each of the antibodies in a panel has been produced by transfer of all six CDRs from a donor antibody, i.e. three heavy chain CDRs and three light chain CDRs.

The CDRs from a donor monoclonal antibody can be incorporated into a human acceptor sequence utilizing molecular biology methods known to the person skilled in the art. Other techniques include those described by de Wildt et al., 1997, J. Immunol. Methods, 207:61-67 and Lagerkvist et al., 1995, BioTechniques 18(5):862-869. Thus, humanized antibodies may be prepared as known in the art by transferring at least one of the CDRs of an individual donor antibody onto a human acceptor framework. The CDRs may be grafted onto any appropriate acceptor variable region framework sequence having regard to the class/type of the donor antibody from which the CDRs are derived, and include primate and human framework regions.

For obtaining humanized antibodies, the "appropriate" framework regions are human variable framework regions. Examples of appropriate human frameworks that can be used in the present invention are KOL, NEWM, REI, EU, TUR, TEI, LAY and POM (Kabat et al., above). Alternatively, human germline sequences may be used. These are available from the MRC Vbase database available at: http://www.mrc-cpe.cam.ac.uk/, entering the term "vbase" in the site search link and accessing the vbase link. Appropriate human frameworks can also be obtained from a database of human immunoglobulin sequences including a database or rearranged IgG sequences 'normal' individuals of diverse ethnic origin.

In the present invention, the acceptor antibody preferably has chains homologous to the donor antibody which are, accordingly, the most appropriate framework; see, for example, WO 90/07861 where Queen proposes that one criterion for the selection of an appropriate framework is to select a framework which is unusually homologous to the donor antibody. Alternatively, a consensus variable region framework from many human antibodies may be selected as the most appropriate framework. In one embodiment, the acceptor heavy and light chains are not derived from the same antibody but may, if desired, comprise composite chains having variable region framework regions derived from different chains, which are, thus, the most appropriate framework.

While the alignments provide sequence identity, it will be appreciated that some differences between donor and acceptor are more likely to be accepted than others on the grounds of residue similarity (for example, size or charge). Thus, it is possible to select an acceptor variable framework sequence which is not the best identity match, but which has conservative or semi-conservative amino acid changes. Thus, the amino acids glycine, alanine, valine, leucine and isoleucine can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include, but are not limited to:

phenylalanine, tyrosine and tryptophan (amino acids having aromatic side chains);

lysine, arginine and histidine (amino acids having basic side chains);

asparagine and glutamine (amino acids having amide side chains);

serine and threonine (amino acids having a hydroxy side chain); and cysteine and methionine (amino acids having sulphur-containing side chains).

In a specific embodiment of the present invention, the most appropriate variable region framework can be selected by taking into account the homology of a human acceptor framework with the donor sequence, but more importantly, selecting those variable region frameworks in which specific residues, being obligatory donor residues, are taken into account, i.e. given weighting (see Table 1). Thus, the more of these weighted (important) donor residues which are already present in a homologous human framework, the more appropriate the human framework is regardless of whether the overall homology is somewhat less than another framework with fewer weighted residues matching. One skilled in the art will therefore appreciate that a different framework may be selected as "appropriate" for each individual donor antibody.

Accordingly, the invention further provides a method for selecting an appropriate human $V_H$ region acceptor sequence, comprising:
(i) performing a homology alignment between a donor $V_H$ sequence and human $V_H$ region sequences; and
(ii) selecting those human sequences which share identity with the donor sequence at least four residues selected from the group consisting of residues 24, 49, 71, 73, 78 and 93, numbered according to the Kabat numbering system.

Preferably, the number of residues (Tier 1H residues; see Table 1) with shared identity in step (ii), above, for the $V_H$ region is five, and most preferably all six residues share identity.

It will be understood by the person skilled in the art that 'weighting' refers to importance such that Tier 1 residues are the most important followed by Tier 2 residues, and so on (see Table 1). In this way, those acceptor sequences that match the minimum number of Tier 1 residues are selected as appropriate. Consequently, it will be apparent that more than one acceptor sequence may be selected as appropriate after homology alignment.

Thus, where multiple appropriate $V_H$ frameworks are apparent, i.e. have the same number of identities, weighting is given to a second subset of residues. Accordingly, the selection of an appropriate human $V_H$ acceptor framework sequence may further comprise:
(iii) assessing the homology between the donor $V_H$ sequence and two or more human sequences selected in step (ii), above; and
(iv) selecting those human sequences which share identity with the donor sequence at least twenty-two residues selected from the group consisting of residues 1, 2, 3, 4, 6, 7, 11, 23, 25, 36, 37, 38, 39, 41, 44, 45, 46, 47, 48, 67, 69, 76, 87, 89, 91 and 94, numbered according to the Kabat numbering system.

Preferably, the number of residues in Tier 2H with shared identity in step (iv), above, for the $V_H$ region is twenty-three, even more preferably twenty-four residues or twenty-five residues, and, most preferably, all twenty-six residues share identity.

More preferably, the number of residues in Tier 2H with shared identity in step (iv), above, for the $V_H$ region is twenty-two or twenty-three, even more preferably twenty-four residues or twenty-five residues, and, most preferably, all twenty-six residues share identity.

In a specific example, different weighting may be given to the Tier 2H residues of step (iv), above, thus splitting Tier 2H into two; Tier 2H' and Tier 3H (see Table 1). Thus, where multiple appropriate $V_H$ frameworks are apparent, i.e. two or more sequences have the same number of identities, weighting is given to a second subset of residues (Tier 2H'). Accordingly, the selection of an appropriate human $V_H$ acceptor framework sequence may further comprise:
(v) assessing the homology between the donor $V_H$ sequence and two or more human sequences selected in step (ii), above; and
(vi) selecting those human sequences which share identity with the donor sequence at least seven residues selected from the group consisting of 36, 37, 39, 45, 47, 48, 76, 89, 91 and 94, numbered according to the Kabat numbering system.

Preferably, the number of residues with shared identity in step (iv), above, for the $V_H$ region is eight or nine, and most preferably all ten residues share identity.

Where multiple appropriate $V_H$ frameworks are again apparent, i.e. have the same number of identities, weighting is given to the third subset of residues (Tier 3H). Accordingly, the method may further comprise:
(vii) assessing the homology between the donor $V_H$ sequence and two or more human sequences selected in step (vi), above; and
(viii) selecting those human sequences which share identity with the donor sequence at least thirteen residues selected from the group consisting of 1, 2, 3, 4, 6, 7, 11, 23, 25, 38, 41, 44, 46, 67, 69 and 87 numbered according to the Kabat numbering system.

Preferably, the number of residues with shared identity in step (viii), above, for the $V_H$ region is fourteen or fifteen, and most preferably all sixteen residues share identity.

Further provided by the present invention is a method for selecting an appropriate human $V_L$ acceptor sequence according to part (2), above, comprising:
(ix) performing a homology alignment between a donor $V_L$ sequence and human $V_L$ framework sequences;
(x) selecting those human sequences which share identity with the donor sequence at least two residues selected from the group consisting of 46, 48 and 58, numbered according to the Kabat numbering system.

Most preferably, the number of residues with shared identity in step (x), above, is all three residues (Tier 1 L residues).

Where multiple appropriate $V_L$ frameworks are apparent, i.e. have the same number of identities, weighting is given to a second subset of residues (Tier 2L). Thus, the selection of an appropriate human $V_L$ acceptor framework sequence may further comprise:

(xi) assessing the homology between the donor $V_L$ sequence and two or more human sequences selected in step (x), above;

(xii) selecting those human sequences which share identity with the donor sequence at least twenty-one residues selected from the group consisting of 1, 2, 3, 4, 6, 35, 36, 37, 38, 44, 45, 47, 49, 60, 62, 63, 64, 65, 66, 67, 68, 69, 70, 71, 85 and 87, numbered according to the Kabat numbering system.

More preferably, the number of residues in Tier 2L with shared identity in step (xii), above, for the $V_L$ region is twenty-two or twenty-three residues, even more preferably twenty-four or twenty-five residues, and most preferably all twenty-six residues share identity.

In a specific example, different weighting may be given to the Tier 2L residues of step (xii), above, thus splitting Tier 2L into two; Tier 2L' and Tier 3L (see Table 1). Thus, where multiple appropriate $V_L$ frameworks are apparent, i.e. two or more sequences have the same number of identities, weighting is given to a second subset of residues (Tier 2L'). Accordingly, the selection of an appropriate human $V_L$ acceptor framework sequence may further comprise:

(xiii) assessing the homology between the donor $V_L$ sequence and two or more human sequences selected in step (x), above; and (xiv) selecting those human sequences which share identity with the donor sequence at least fifteen residues selected from the group consisting of 2, 6, 35, 36, 38, 44, 49, 62, 63, 64, 65, 66, 67, 68, 69, 71, 85 and 87, numbered according to the Kabat numbering system.

More preferably, the number of residues with shared identity in step (xiv), above, for the $V_L$ region is sixteen or seventeen residues. Most preferably all eighteen residues share identity.

Where multiple appropriate $V_L$ frameworks are again apparent, i.e. have the same number of identities, weighting is given to a third subset of residues. Accordingly, the method may further comprise:

(xv) assessing the homology between the donor $V_L$ sequence and two or more human sequences selected in step (xiv), above; and (xvi) selecting those human sequences which share identity with the donor sequence at least six residues selected from the group consisting of 1, 3, 4, 37, 45, 47, 60 and 70, numbered according to the Kabat numbering system.

Preferably, the number of residues with shared identity in step (xvi), above, for the $V_L$ sequence is at least seven. Most preferably all eight residues share identity.

TABLE 1

| Tier | Tier Residue; numbered according to Kabat |
| --- | --- |
| 1H | 24, 49, 71, 73, 78, 93 |
| 2H | 1, 2, 3, 4, 6, 7, 11, 23, 25, 36, 37, 38, 39, 41, 44, 45, 46, 47, 48, 67, 69, 76, 87, 89, 91, 94 |
| 2H' | 36, 37, 39, 45, 47, 48, 76, 89, 91, 94 |
| 3H | 1, 2, 3, 4, 6, 7, 11, 23, 25, 38, 41, 44, 46, 67, 69, 87 |
| 1L | 46, 48, 58 |

TABLE 1-continued

| Tier | Tier Residue; numbered according to Kabat |
| --- | --- |
| 2L | 1, 2, 3, 4, 6, 35, 36, 37, 38, 44, 45, 47, 49, 60, 62, 63, 64, 65, 66, 67, 68, 69, 70, 71, 85, 87 |
| 2L' | 2, 6, 35, 36, 38, 44, 49, 62, 63, 64, 65, 66, 67, 68, 69, 71, 85, 87 |
| 3L | 1, 3, 4, 37, 45, 47, 60, 70 |

H = heavy chain; L = light chain

In a most preferred embodiment, the alignments and matching are performed in one step, preferably in an automated manner. A standard BLAST as known in the art may be used. Thus, a computer program may be used to identify the shared residues within Tiers 1 to 3, above, giving the greatest weighting to the Tier 1 residues and lesser weighting to those Tier 2 residues. Thus, the methods of the invention can be performed manually, consecutively or sequentially, and most preferably, in an automated manner (e.g. using a computer), consecutively or sequentially.

In another embodiment, the greatest weighting is given to Tier 1 residues with lesser weighting given to Tier 2' residues and the least weighting to Tier 3 residues. Accordingly, it should be understood by those skilled in the art that the better match, i.e. the most appropriate sequence will be that sequence(s) which matches all Tier 1H or 1L. Several matches requires $2^{nd}$ Tier alignment, i.e. at least 21 Tier 2H or 22 Tier 2L residues. An even better match will be that sequence which matches all Tier 1H or 1L residues, and 23, 24 or 25 Tier 2H, or 22, 23, 24 or 25 Tier 2L residues. The best match will be that sequence which matches all Tier 1H or 1L residues, and all Tier 2H or 2L residues. The same reasoning applies where three Tiers are given. In the case where there are still two or more appropriate frameworks, that sequence with the greatest homology between the non-Tier residues will generally be the best framework sequence.

The above procedures can be used to select an appropriate variable region acceptor framework, or frameworks, which comprise(s) frameworks 1, 2 and 3. Framework 4 is provided by the J-region. An appropriate human J-region sequence can be selected by a similar alignment method. Many of the important framework 4 residues tend to be conserved between species (e.g. heavy chain Kabat numbered residues 103, 104 and 106; light chain Kabat numbered residues 98, 99 and 101), so there is less of a need to weight certain residues more than others. A simple identity alignment can be used to select the most similar human J-region sequence, as will be clear to the person skilled in the art. Preferably, a J-region sequence which forms the C-terminal end of CDR-H3 and CDR-L3 is used in these alignments to select the closest human J-region.

In a specific example, where not all of the human acceptor framework residues within a given Tier match the donor sequence, those residues not matching may be altered to match the donor, i.e. a transfer of donor residue to acceptor sequence. Thus, for example but without limitation, if in Tier 1H residues 24 and 93 of the acceptor sequence do not match the donor sequence, transfer of donor residues 24 and/or 93 may be performed to alter the acceptor sequence. The latter is merely an example and not meant be limiting in any way. Accordingly, the methods of the invention can further comprise altering one or more non-matching acceptor residues in any Tier to match the donor sequence.

Thus, a particular advantage of the present invention is apparent especially where the number of donor antibodies with specificity for the selected antigen is large, for example but without limitation, more than 20, 30, 40, 50 or more antibodies, then those antibodies can be filtered by performing one or more homology alignments with human frameworks, with weighting given to those with residues in Tiers 1H, 2H, 2H', 3H, 1L, 2L, 2L' and 3L, above. Thus, those donor antibodies with fewer identities, i.e. those with the fewest matches within a Tier or Tiers, can be filtered out, leaving the person skilled in the art with those antibodies with the better/best matches for use in making up the panel of humanized antibodies. In this way, the invention provides a robust means of selecting those donor antibodies for which appropriate frameworks can be found. Those with poor matches using the selection methods described can be discarded. The methods are, thus, particularly useful in selecting those donor antibodies which can be subjected to CDR-only transfer. The whole process of humanization is made simpler and easier as minimal grafting is required (minimally 1, 2, 3, 4, 5, or preferably all 6 CDRs from the donor species).

Accordingly provided is a method for obtaining humanized antibodies with specificity for a selected antigen comprising:

(1) providing multiple donor antibody $V_H$ and/or $V_L$ region sequences, each with specificity for the selected antigen;
(2a) selecting an appropriate human framework $V_H$ acceptor region sequence for each donor sequence wherein said selection comprises performing a homology alignment between a donor $V_H$ sequence and human $V_H$ region sequences and selecting those human sequences which:
  (i) share identity with the donor sequence at least four residues selected from a group of six residues consisting of residues 24, 49, 71, 73, 78 and 93, numbered according to the Kabat numbering system; and
  (ii) optionally share identity with the donor sequence at least twenty-two selected from the group consisting of 1, 2, 3, 4, 6, 7, 11, 23, 25, 36, 37, 38, 39, 41, 44, 45, 46, 47, 48, 67, 69, 76, 87, 89, 91 and 94, numbered according to the Kabat numbering system; and/or
(2b) selecting an appropriate human framework $V_L$ acceptor region sequence for each donor sequence wherein said selection comprises performing a homology alignment between a donor $V_L$ sequence and human $V_L$ framework sequences and selecting those human sequences which:
  (i) share identity with the donor sequence at least two residues selected from the group consisting of 46, 48 and 58, numbered according to the Kabat numbering system;
  (ii) optionally share identity with the donor sequence at least twenty-one residues selected from the group consisting of 1, 2, 3, 4, 6, 35, 36, 37, 38, 44, 45, 47, 49, 60, 62, 63, 64, 65, 66, 67, 68, 69, 70, 71, 85 and 87, numbered according to the Kabat numbering system;
(3) transferring at least one CDR selected from the $V_H$ and/or $V_L$ region of each donor antibody onto each of the selected appropriate human framework sequences to obtain a panel of humanized antibody sequences;
(4) optionally, transferring one or more of any non-matched donor residues of parts (2a) and/or (2b) onto the selected human framework sequences;
(5) expressing each humanized antibody sequence;
(6) screening the expressed sequences for antigen-binding activity; and
(7) selecting at least one high affinity humanized antibody.

In a preferred embodiment, the present invention provides a method for obtaining humanized antibodies with specificity for a selected antigen comprising:

(1) providing multiple donor antibody $V_H$ and/or $V_L$ region sequences, each with specificity for the selected antigen;
(2a) selecting an appropriate human framework $V_H$ acceptor region sequence for each donor sequence wherein said selection comprises performing a homology alignment between the donor $V_H$ sequence and human $V_H$ region sequences and selecting those human sequences which:
  (i) share identity with the donor sequence at least four residues selected from a group of six residues consisting of residues 24, 49, 71, 73, 78 and 93, numbered according to the Kabat numbering system;
  (ii) additionally share identity with the donor sequence at least seven residues selected from the group consisting of 36, 37, 39, 45, 47, 48, 76, 89, 91 and 94, numbered according to the Kabat numbering system; and
  (iii) optionally share identity with the donor sequence at least thirteen residues selected from the group consisting of 1, 2, 3, 4, 6, 7, 11, 23, 25, 38, 41, 44, 46, 67, 69 and 87, numbered according to the Kabat numbering system; and/or
(2b) selecting an appropriate human framework $V_L$ acceptor region sequence for each donor sequence wherein said selection comprises performing a homology alignment between a donor $V_L$ sequence and human $V_L$ sequences and selecting those human sequences which:
  (i) share identity with the donor sequence at least two residues selected from the group consisting of 46, 48 and 58, numbered according to the Kabat numbering system;
  (ii) additionally share identity with the donor sequence at least fifteen residues selected from the group consisting of 2, 6, 35, 36, 38, 44, 49, 62, 63, 64, 65, 66, 67, 68, 69, 71, 85 and 87, numbered according to the Kabat numbering system; and
  (iii) optionally share identity with the donor sequence at least six residues selected from the group consisting of 1, 3, 4, 37, 45, 47, 60 and 70, numbered according to the Kabat numbering system;
(3) transferring at least one CDR selected from the $V_H$ and/or $V_L$ region of each donor antibody onto each of the selected appropriate human framework sequences to obtain a panel of humanized antibody sequences;
(4) optionally, transferring one or more of any non-matched donor residues of parts (i), (ii), and/or (iii) onto the selected framework sequences;
(5) expressing each humanized antibody sequence;
(6) screening the expressed sequences for antigen-binding activity; and
(7) selecting at least one high affinity humanized antibody.

Preferably, the panel of antibodies used in the methods of the invention has specificity for one antigen, i.e. the antigen used to raise the in vivo immune response. In one embodiment, different antibodies have specificity for different selected antigens.

After CDR-transfer the antibodies can be screened for antigen-binding activity and an appropriate high affinity antibody can be selected. Antigen-binding activity is intended to include not only affinity, but also to an activity, such as antibody dependent cell-mediated cytotoxicity (ADCC) and/or complement dependent cytotoxicity (CDC), blocking activity, for example blocking of ligand binding, or blocking of activity of the antigen directly, or indirectly, for example by blocking of a downstream pathway in which the antigen is involved. It is also intended to include stimulatory activity such as stimulation of antigen activity, directly or indirectly.

Most preferably, the methods of the invention utilize humanized antibodies that are expressed efficiently, for example expressed efficiently in E. Coli and/or in mammalian cells. Thus, when selecting a high affinity antibody, the ability of that antibody to be expressed efficiently can be taken into account. Accordingly, the panel of humanized antibodies may be filtered by excluding poorly-expressed antibodies.

As used herein, 'well-expressed' includes humanized antibody which are expressed at a concentration of at least 250 mg to 500 mg per liter of fermentation, for example per liter of microbial fermentation, and 500 mg to 1000 mg or more per liter mammalian cells.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing. Any suitable host cell/vector system may be used for expression of the DNA sequences encoding the antibody molecules. Bacterial, for example E. coli, and other microbial systems may be used or eukaryotic, for example mammalian, host cell expression systems may also be used. Suitable mammalian host cells include CHO and NSO. Cell lines may transiently or stably express the humanized antibody molecules. The types of expression systems available to produce the humanized antibody molecules include bacterial, yeast, insect and mammalian expression systems, the methods for which are well known in the art (Verma et al., 1998, J. Immunol. Methods, 216, 165-181; Simmons et al., J. Immunol. Methods, 2002, 263, 133-147), the contents of which, including referenced articles, are incorporated in their entirety.

Expression of antibodies may be performed as is readily known in the art. In one example, the appropriate vectors contain heavy and/or light chain constant regions or parts thereof such that whole antibodies or antibody fragments, such as Fab or Fab' may be produced. With each $V_L$ and/or $V_H$ in separate vectors it is possible to readily co-transfect each $V_H$ and/or $V_L$ combination into CHO cells. For example, the V-region may be sub-cloned into the expression vectors pMRR10 and pMRR14 (see, for example, WO2004/072116). These are separate vectors for expression of the light and/or heavy chain respectively and contain genomic DNA encoding constant region genes for human kappa light chain and gamma-4 heavy chain, respectively. These vectors may then be co-transfected into CHO cells and whole antibodies produced by culturing the CHO cells.

Alternatively, each $V_H$ and $V_L$ pair may be expressed in the same vector either as whole antibodies or as fragments, including scFvs.

The term 'affinity' as used herein refers to the strength with which the antibody binds to the selected antigen. High affinity antibodies have a low dissociation rate constant. The antibodies selected using the methods of the invention have a high affinity for the selected antigen. Preferably, high affinity antibodies include antibodies with an affinity in the nanomolar range, and more preferably in the picomolar range. More preferably, the antibodies selected using the methods of the invention have an affinity for the selected antigen in the range of 1 pM, or less, to 10 nM, even more preferably in the range 1 pM, or less, to 500 pM, and most preferably 1 pM, or less, to 200 pM.

The affinity of an antibody and the dissociation rate of an antibody-antigen interaction can be determined by using methods well known in the art, such as BIAcore analysis or competitive binding assays. Thus, screening and selection of parts (i) and (ii), above, i.e. concerning the antigen-binding activity, may be performed using these methods. One example of a competitive binding assay is a radioimmunoassay comprising the incubation of radio-labelled antigen (e.g. 3H or 125I) with the antibody of interest in the presence of increasing amounts of unlabelled antigen, and the detection of the antibody bound to the labelled antigen. The affinity of the antibody of interest for a particular antigen and the binding off-rates can be determined from the data by Scatchard plot analysis. Preferably BIAcore is used to determine the affinity of the antibodies of the present invention. BIAcore is an automated biosensor system that can be used to measure molecular interactions (Karlsson, et al., 1991, J. Immunol. Methods, 145, 229-240). In this method, the concentration of antigen does not in many cases need to be accurately determined, and it is possible to obtain dissociation-rate measurements for already high affinity antibodies.

ADCC and CDC can be measured as known in the art, for example by observing cell killing in the presence of test antibody compared to a control antibody.

EXAMPLES

1. Preparation of a Panel of Humanized Antibodies

CDR-Grafted Antibodies

Rat were immunised with a human protein, antigen X (hX) and B cells prepared. These were subjected to SLAM and 77 antibodies were isolated. This can be performed as described in Babcook et al., 1996, Proc. Natl. Acad. Sci, 93, 7843-7848, and WO 92/02551, with screening assays as described in WO2004/051268, WO2004/106377, WO2005/019823. The CDRs of the light and heavy chain gene V-region sequences were transferred to appropriate human frameworks which were selected using weightings s for Tier 1H, 2H and 1 L and 2L Tier residues. From a panel of 29 anti-hX antibodies isolated by the SLAM process, 15 were chosen for CDR-only transfer. Four high affinity antibodies were obtained from the 15. For the other 14 mAbs grafts were made containing at least 1 donor residue.

Table 2 indicates the number of residues matched by performing the homology alignment according to the methods of the invention between the donor heavy chain antibody variable region sequences and human antibody heavy chain variable region framework sequences of 4 antibodies obtained from the panel of twelve.

TABLE 2

Donor Identities with Human Acceptor Framework Residues

| Anti-X antibody | Framework | Number of Residues | | |
|---|---|---|---|---|
| | | Tier 1 | Total of Tier 1 & 2 | Tier 2 |
| 71b | VH3 1-3 3-07 | 6/6 | 30/32 | 24/26 |
| | VK1 2-1-(1) O12 | 2/3 | 23/29 | 21/26 |
| 271b | VH3 1-3 3-07 | 6/6 | 28/32 | 22/26 |
| | VK1 2-1-(1) O12 | 3/3 | 24/29 | 21/26 |
| 1160b | VH3 1-3 3-23 | 5/6 | 27/32 | 22/26 |
| | VK1 2-1-(1) O12 | 3/3 | 24/29 | 21/26 |
| 1189 | VH3 1-3 3-07 | 6/6 | 30/32 | 24/26 |
| | VK1 2-1-(1) O12 | 2/3 | 24/29 | 22/26 |

2. Expression of Humanized IgG

CDR-Only Grafted Antibodies

The light chain gene V-region sequence was sub-cloned into the UCB-Celltech human light chain expression vector pKH10.1, which contains DNA encoding the human C-Kappa constant region (Km3 allotype), expressed from the hCMV promoter. The heavy chain V-region sequence was sub-cloned into the UCB-Celltech in-house human gamma-4 expression vector pVhg4P FL, which contains DNA encoding the human gamma-4 constant region containing the hinge stabilising mutation S241P (Angal et al., Mol. Immunol. 1993, 30(1): 105-8). This vector also employs the hCMV promoter. Co-transfection of these plasmids into CHO cells results in the expression of the humanized antibody.

3. Expression of Humanized Fabs

CDR-Only Grafted Fabs

DNA was synthesised encoding a humanised light chain (with the Km3 allotype of the kappa constant region), an intergenic sequence and a humanised $V_H$ sequence. This was sub-cloned into the UCB-Celltech in-house expression vector pTTOD(Fab) (a derivative of pTTO-1, described in Popplewell et al., Methods Mol. Biol. 2005; 308: 17-30) which contains DNA encoding the human gamma-1 CH1 constant region. This gave rise to a dicistronic gene arrangement consisting of the gene for the humanised light chain followed by the gene for the humanised heavy chain Fab fragment, under the control of the tac promoter. The recombinant expression plasmid was transformed into the *E. coli* strain W3110 in which expression is induced by addition of IPTG. Expression experiments were performed at small scale initially (5 ml culture volumes) with addition of 200 μM IPTG at OD (600 nm) of approx. 0.5, cells were harvested 2 hours post induction and extracted overnight at 30° C. in Tris/EDTA. Clarified extracts were used for affinity analysis by Biacore. Constructs giving promising expression yields and activities were selected for fermentation.

4. Biacore Assay for Anti-Human Antigen X (Anti-X)

Biacore (Biacore 3000; Biacore AB) analysis of anti-X Fab and IgG samples prepared by CDR-only transfer of rat variable region heavy and light chain CDRs onto human framework regions was performed. The assay format was capture of the anti-X sample by immobilised anti-X IgG then titration of hX over the captured surface.

Affinipure goat anti-human IgG (Jackson ImmunoResearch) was immobilised on a CM5 Sensor Chip (Flowcell 2) via amine coupling chemistry to a level of 6000-7000RU. HBS-EP buffer (10 mM HEPES, pH 7.4, 0.15M NaCl, 3 mM EDTA, 0.005% Surfactant P20, Biacore AB) was used as the running buffer with a flow rate of 10 μl/min for capture of the anti-hX sample, 30 μl/min for binding of hX and 10 μl/min for regeneration.

An injection of the anti-hX sample was performed to give a capture level of approximately 200 RU on the immobilised anti-human IgG. Human X was titrated over the captured anti-hX surface at various concentrations. The surface was regenerated by a 10 μl injection of 40 mM HCl followed by a 5 μl injection of 5 mM NaOH. Anti-hX sample and hX were passed over a blank control surface (Flowcell 1) prior to the anti-hIgG and the resultant sensorgram was the response on Flowcell 2–the response on Flowcell 1.

The sensorgram for hX binding was corrected with the control buffer sensorgram. Kinetic parameters were calculated using BIA evaluation 3.2 software.

The affinity and dissociation constants of both the anti-X Fab and IgG samples are shown in Tables 3a and 3b, respectively. The results show that from a panel of 12 antibodies 2 high affinity Fabs and 2 high affinity IgGs were selected. The affinity of these antibodies is such that they may be used as potential therapeutic candidates.

TABLE 3a

Affinity of antibodies to antigen hX - Fab Samples

| Anti-hX | $k_a$ (M$^{-1}$s$^{-1}$) | $k_d$ (s$^{-1}$) | $K_D$ (M) | KD (pM) |
|---|---|---|---|---|
| 71b | 2.44E+06 | 1.39E−04 | 5.70E−11 | 57 |
| 271b | 2.03E+06 | 5.14E−05 | 2.53E−11 | 25 |

TABLE 3b

Affinity of antibodies to antigen hX - IgG Samples

| Anti-hX | $k_a$ (M$^{-1}$s$^{-1}$) | $k_d$ (s$^{-1}$) | $K_D$ (M) | KD (pM) |
|---|---|---|---|---|
| 1160b | 1.53E+06 | 5.26E−05 | 3.44E−11 | 34 |
| 1189 | 2.36E+06 | 9.66E−05 | 4.09E−11 | 41 |

Of the 12 CDR-only grafts, 4 high affinity antibodies were selected. The affinities of all four were less than 60 pM (see Tables 2 and 3a & b, above).

The invention claimed is:

1. A method for obtaining at least one humanized antibody with specificity for a selected antigen comprising:
   (a) providing multiple donor antibody $V_H$ and/or $V_L$ region sequences each with specificity for the selected antigen;
   (b) selecting for each donor region sequence of step (a), an appropriate human $V_H$ region acceptor framework sequence and/or an appropriate human $V_L$ region acceptor framework sequence, wherein selection of the human acceptor framework is on the basis of those frameworks where weighted donor residues are already present, regardless of whether the overall sequence homology is less than that of another framework with fewer weighted residues are matching;
   (c) transferring CDR-H1, CDR-H2, CDR-H3, CDR-L1, CDR-L2 and CDR-L3 of each donor antibody region sequence onto each of the selected appropriate human acceptor framework sequences to obtain a panel of humanized antibody sequences,
       wherein the panel of humanized antibody sequences comprises at least five antibodies;
       wherein only the CDRs of each donor antibody region sequence are transferred onto each of the selected appropriate human acceptor framework sequences;
   (d) expressing the humanized antibody sequences;
   (e) screening the expressed humanized antibody sequences for antigen-binding activity; and
   (f) selecting at least one screened high affinity humanized antibody sequence;
       wherein the method does not comprise selecting candidate residues of the human acceptor framework sequences for back mutation to donor antibody residues.

2. The method according to claim 1, wherein the selection of part (b) comprises performing a homology alignment between the donor $V_H$ sequence and human $V_H$ region acceptor sequences, and/or the donor $V_L$ sequence and human $V_L$ region acceptor sequences and selecting those human acceptor sequences which:
   (I) f or $V_H$:
       (i) share identity with the donor sequence at, at least, four residues selected from a group of six residues consisting of residues 24, 49, 71, 73, 78 and 93, numbered according to the Kabat numbering system; and
(ii) share identity with the donor sequence at, at least, twenty-two residues selected from the group consisting of 1, 2, 3, 4, 6, 7, 11, 23, 25, 36, 37, 38, 39, 41, 44, 45, 46, 47, 48, 67, 69, 76, 87, 89, 91 and 94, numbered according to the Kabat numbering system; and/or
(II) f or $V_L$ (Kappa):
(i) share identity with the donor sequence at, at least, two residues selected from the group consisting of 46, 48 and 58, numbered according to the Kabat numbering system; and
(ii) share identity with the donor sequence at, at least, twenty-one residues selected from the group consisting of 1, 2, 3, 4, 6, 35, 36, 37, 38, 44, 45, 47, 49, 60, 62, 63, 64, 65, 66, 67, 68, 69, 70, 71, 85 and 87, numbered according to the Kabat numbering system.

3. The method according to claim 1, wherein selection of part (b) comprises performing a homology alignment between a donor $V_H$ sequence and human $V_H$ region acceptor sequences, and/or the donor $V_L$ sequence and human $V_L$ region acceptor sequences and selecting those human acceptor sequences which:
(I) f or $V_H$:
(i) share identity with the donor sequence at, at least, four residues selected from a group of six residues consisting of residues 24, 49, 71, 73, 78 and 93, numbered according to the Kabat numbering system;
(ii) additionally share identity with the donor sequence at, at least, seven residues selected from the group consisting of 36, 37, 39, 45, 47, 48, 76, 89, 91 and 94, numbered according to the Kabat numbering system; and
(iii) share identity with the donor sequence at, at least, fourteen residues selected from the group consisting of 1, 2, 3, 4, 6, 7, 11, 23, 25, 38, 41, 44, 46, 67, 69 and 87, numbered according to the Kabat numbering system; and/or
(II) f or $V_L$ (Kappa):
(i) share identity with the donor sequence at, at least, two residues selected from the group consisting of 46, 48 and 58, numbered according to the Kabat numbering system;
(ii) additionally share identity with the donor sequence at, at least, fifteen residues selected from the group consisting of 2, 6, 35, 36, 38, 44, 49, 62, 63, 64, 65, 66, 67, 68, 69, 71, 85 and 87, numbered according to the Kabat numbering system; and
(iii) share identity with the donor sequence at, at least, six residues selected from the group consisting of 1, 3, 4, 37, 45, 47, 60 and 70, numbered according to the Kabat numbering system.

4. The method of claim 1, wherein the panel of humanized antibodies all have specificity for the same selected antigen.

5. A humanized antibody produced by the method of claim 1.

6. The method of claim 2, wherein the panel of humanized antibodies all have specificity for the same selected antigen.

7. The method of claim 3, wherein the panel of humanized antibodies all have specificity for the same selected antigen.

8. A humanized antibody produced by the method of claim 2.

9. A humanized antibody produced by the method of claim 3.

10. A method for obtaining at least one humanized antibody with specificity for a selected antigen comprising:
(a) providing multiple donor antibody $V_H$ and/or $V_L$ region sequences each with specificity for the selected antigen;
(b) selecting an appropriate human $V_H$ and/or $V_L$ region acceptor framework sequence for each donor sequence, wherein the selection comprises performing a homology alignment between the donor $V_H$ sequence and human $V_H$ region acceptor sequences, and/or the donor $V_L$ sequence and human $V_L$ region acceptor sequences and selecting those human acceptor sequences which:
(I) f or $V_H$:
(i) share identity with the donor sequence at, at least, five residues selected from a group of six residues consisting of residues 24, 49, 71, 73, 78 and 93, numbered according to the Kabat numbering system; and
(ii) share identity with the donor sequence at, at least, twenty-two residues selected from the group consisting of 1, 2, 3, 4, 6, 7, 11, 23, 25, 36, 37, 38, 39, 41, 44, 45, 46, 47, 48, 67, 69, 76, 87, 89, 91 and 94, numbered according to the Kabat numbering system; and/or
(II) f or $V_L$ (Kappa):
(i) share identity with the donor sequence at, at least, two residues selected from the group consisting of 46, 48 and 58, numbered according to the Kabat numbering system; and
(ii) share identity with the donor sequence at, at least, twenty-one residues selected from the group consisting of 1, 2, 3, 4, 6, 35, 36, 37, 38, 44, 45, 47, 49, 60, 62, 63, 64, 65, 66, 67, 68, 69, 70, 71, 85 and 87, numbered according to the Kabat numbering system;
(c) transferring CDR-H1, CDR-H2, CDR-H3, CDR-L1, CDR-L2 and CDR-L3 of each donor antibody onto each of the selected appropriate human acceptor framework sequences to obtain a panel of humanized antibody sequences,
wherein the panel of humanized antibody sequences comprises at least five antibodies;
wherein only the CDRs of each donor antibody are transferred onto each of the selected appropriate human acceptor framework sequences, wherein all humanized antibody sequences of the panel of humanized antibody sequences have specificity for the same selected antigen;
(d) expressing the humanized antibody sequences, wherein only the CDRs of each donor antibody have been transferred;
(e) screening the expressed humanized antibody sequences for antigen-binding activity; and
(f) selecting at least one screened high affinity humanized antibody sequence;
wherein the method does not comprise selecting candidate residues of the human acceptor framework sequences for back mutation to donor antibody residues.

* * * * *